(12) United States Patent
Neumann

(10) Patent No.: US 12,040,072 B2
(45) Date of Patent: Jul. 16, 2024

(54) APPARATUS AND METHOD FOR GENERATING ALIMENTARY DATA WITHIN A GEOFENCE

(71) Applicant: KPN INNOVATIONS, LLC., Lakewood, CO (US)

(72) Inventor: Kenneth Neumann, Lakewood, CO (US)

( * ) Notice: Subject to any disclaimer, the term of this patent is extended or adjusted under 35 U.S.C. 154(b) by 0 days.

(21) Appl. No.: 17/976,387

(22) Filed: Oct. 28, 2022

(65) Prior Publication Data

US 2024/0145063 A1 May 2, 2024

(51) Int. Cl.
*G16H 20/60* (2018.01)
*G16H 50/70* (2018.01)

(52) U.S. Cl.
CPC ............ *G16H 20/60* (2018.01); *G16H 50/70* (2018.01)

(58) Field of Classification Search
CPC ................................ G16H 20/60; G16H 50/70
See application file for complete search history.

(56) References Cited

U.S. PATENT DOCUMENTS

| | | | |
|---|---|---|---|
| 5,527,788 A | 6/1996 | Svec et al. | |
| 2005/0209178 A1 | 9/2005 | Pulst | |
| 2013/0195827 A1 | 8/2013 | Blum | |
| 2014/0343964 A1 | 11/2014 | Yoon | |
| 2017/0116373 A1* | 4/2017 | Ginsburg | G16H 10/40 |
| 2018/0043182 A1* | 2/2018 | Wu | A61N 5/1039 |
| 2018/0113986 A1* | 4/2018 | Zhu | G16H 10/60 |
| 2019/0254331 A1 | 8/2019 | Astrup | |
| 2020/0005928 A1 | 1/2020 | Daniel | |

(Continued)

FOREIGN PATENT DOCUMENTS

| | | |
|---|---|---|
| CH | 713713 | 10/2018 |
| CN | 103667456 | 3/2014 |

(Continued)

OTHER PUBLICATIONS

Shenoy, Usha; Influence of Central Obesity Assessed by Conicity Index on Lung Age in Young Adults; Journal of Clinical and Diagnostic Research; Apr. 2017 (Year: 2017).*

(Continued)

*Primary Examiner* — Michael Tomaszewski
*Assistant Examiner* — Shyam M Goswami
(74) *Attorney, Agent, or Firm* — Caldwell Intellectual Property Law

(57) ABSTRACT

An apparatus for generating alimentary data within a geofence is disclosed. The apparatus comprises a memory and at least a processor. The memory instructs the at least a processor to receive a geofence, wherein the geofence comprises a predetermined geographic area. memory instructs the at least a processor to identify population data as a function of the geofence, wherein the population data comprises at least a statistical markup data. The memory then instructs the processor to calculate an conicity index as a function of the at least a statistical markup data. The memory instructs the processor to generate alimentary data as function of the conicity index, wherein the alimentary data comprises a recommended nutrient intake. The memory then instructs the processor to determine a plurality of phenotype clusters within the geofence as a function of the alimentary data.

10 Claims, 8 Drawing Sheets

(56) References Cited

U.S. PATENT DOCUMENTS

| | | | |
|---|---|---|---|
| 2020/0065681 A1* | 2/2020 | Wolf | G16H 10/40 |
| 2020/0211708 A1 | 7/2020 | Geronimo-Button | |
| 2020/0321123 A1* | 10/2020 | Neumann | G16H 10/60 |
| 2022/0246275 A1* | 8/2022 | Neumann | G16H 70/00 |

FOREIGN PATENT DOCUMENTS

| | | | | |
|---|---|---|---|---|
| RU | 2691145 | | 6/2019 | |
| WO | 0103700 A1 | | 1/2001 | |
| WO | WO-2014091017 A2 * | | 6/2014 | G16B 20/00 |
| WO | 2019074388 | | 4/2019 | |

OTHER PUBLICATIONS

Title: Precision Nutrition: A Review of Personalized Nutritional Approaches for the Prevention and Management of Metabolic Syndrome; By: Toro Martin; Date: 2017.

http://dx.doi.org/10.3746/pnf.2015.20.1.1; Title: Obesity: Interactions of Genome and Nutrients Intake; By: Doo; Date: 2015.

Title: Insulin Receptor Substrate 1 Gene Variation Modifies Insulin Resistance Response to Weight-Loss Diets in a 2-Year Randomized Trial; By: 2011; By: Qibin.

Development of metabolic health assessment: Paving the way to disease prevention through personalized nutrition; By: Zivkovic; Date: Jun. 18, 1996.

* cited by examiner

APPARATUS AND METHOD FOR GENERATING ALIMENTARY DATA WITHIN A GEOFENCE

FIELD OF THE INVENTION

The present invention generally relates to the field of nutrition science in particular, the present invention is directed to an apparatus and method for generating alimentary data within a geofence.

BACKGROUND

Design of systems for analysis of alimentary data is often frustrated by the extreme complexity and variability of the subject matter between subjects. A vast multiplicity of factors to be considered is further complicated by a complex array of subtle, but crucial data. Worse still, a given factor may vary significantly between demographics, and in ways that can frustrate consistent application of alimentary data to analytical techniques.

SUMMARY OF THE DISCLOSURE

In an aspect, an apparatus for generating alimentary data within a geofence is disclosed. The apparatus comprises a memory and at least a processor. The memory contains instructions configuring the at least a processor to receive a geofence, wherein the geofence comprises a predetermined geographic area. memory instructs the at least a processor to identify population data as a function of the geofence, wherein the population data comprises at least a statistical markup data. The memory contains instructions configuring the processor to calculate an conicity index as a function of the at least a statistical markup data. The memory contains instructions configuring the processor to generate alimentary data as function of the conicity index, wherein the alimentary data comprises a recommended nutritional intake. The memory contains instructions configuring the processor to determine a plurality of phenotype clusters within the geofence as a function of the alimentary data.

In another aspect, a method for generating alimentary data within a geofence is disclosed. The method includes receiving, using at least a processor, a geofence, wherein the geofence comprises a predetermined geographic area. The method includes identifying, using the at least a processor, population data as a function of the geofence, wherein the population data comprises at least a statistical markup data. The method then calculates, using the at least a processor, an conicity index as a function of the at least a statistical markup data. The method additionally generates alimentary data as function of the conicity index, wherein the alimentary data comprises a recommended nutritional intake. The method then determines a plurality of phenotype clusters within the geofence as a function of the alimentary data These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to an apparatus and methods for generating alimentary data within a geofence is disclosed. The apparatus comprises a memory and at least a processor. The memory contains instructions configuring the at least a processor to receive a geofence, wherein the geofence comprises a predetermined geographic area. The memory contains instructions configuring the at least a processor to identify population data as a function of the geofence, wherein the population data comprises at least a statistical markup data. The memory contains instructions configuring the processor to calculate an conicity index as a function of the at least a statistical markup data. The memory contains instructions configuring the processor to generate alimentary data as function of the conicity index, wherein the alimentary data comprises a recommended nutritional intake. The memory contains instructions configuring the processor to determine a plurality of phenotype clusters within the geofence as a function of the alimentary data. Exemplary embodiments illustrating aspects of the present disclosure are described below in the context of several specific examples.

Figure 1:
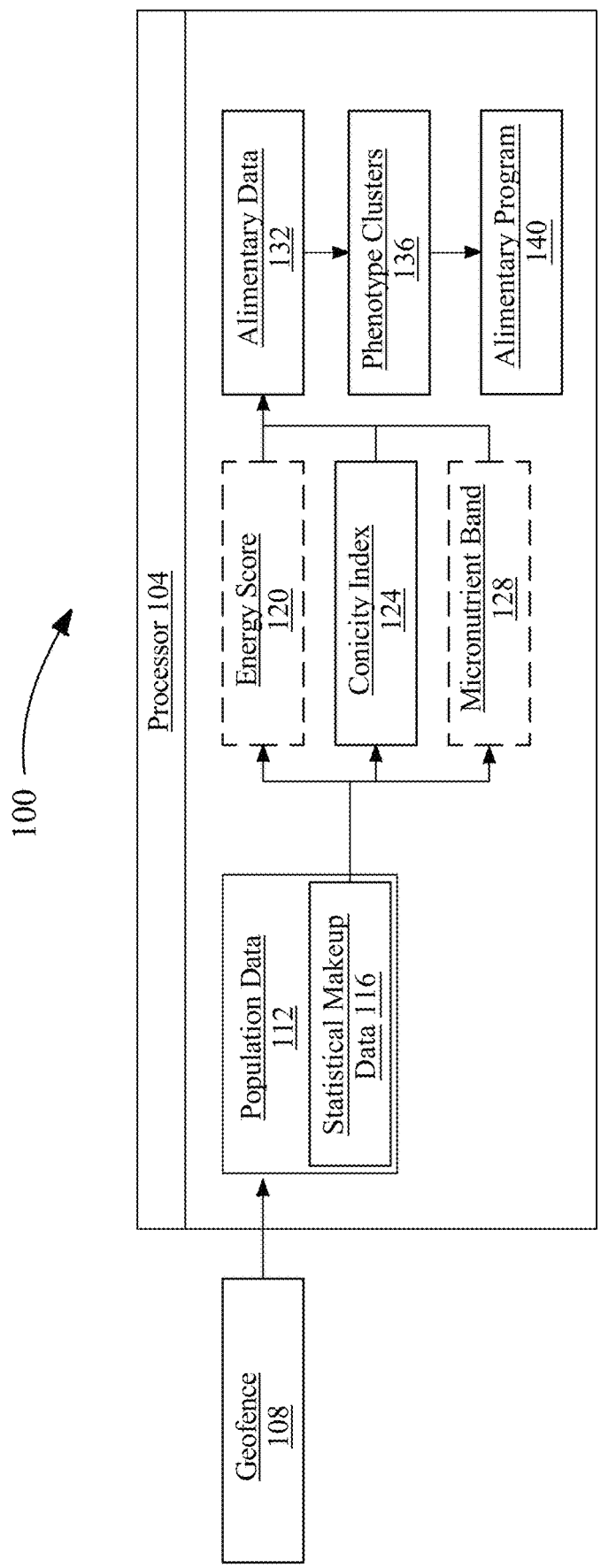
FIG. 1 is a block diagram of an exemplary embodiment of an apparatus for generating alimentary data within a geofence.

Referring now to FIG. 1, an exemplary embodiment of an apparatus 100 for generating alimentary data within a geofence is illustrated. Apparatus 100 includes a processor 104. Processor 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of apparatus 100 and/or computing device.

With continued reference to FIG. 1, apparatus 100 includes a memory communicatively connected to the at least a processor 104. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure. Memory contains instructions configuring the at least a processor 104 to perform one or more steps as discussed throughout this disclosure.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, processor 104 may be configured to receive a geofence 108. As used in the current disclosure, a "geofence" is a virtual perimeter surrounding a real-world geographic area. A geofence 108 may be generated as a radius around a point or location or arbitrary borders drawn by a user. In some embodiments, the point or location may be selected by a user through user input, wherein user input may include, as non-limiting examples, tapping on a screen, inputting an address, inputting coordinates, and the like. A geofence 108 additionally be generated to match a predetermined set of boundaries such as neighborhoods, school zones, zip codes, county, state, and city limits, area codes, voting districts, geographic regions, streets, rivers, other landmarks, and the like. In embodiments, geofences may be generated as a function of a user input.

With continued reference to FIG. 1, processor 104 may identify population data 112 as a function of the geofence. As used in the current disclosure, "population data" is data concerning the enumeration of humans located a given area. Population data 112 may be generated from a database. In embodiments, once the geofence 108 is identified population data 112 may generated using public records, such as the U.S. Census data. In other embodiments, population data 112 may be generated as a function of population sampling and the geofence 108. As used in the current disclosure, "Population sampling" is the e the selection of a subset (a statistical sample) of individuals from within a statistical population to estimate characteristics of the whole population. Population sampling may require the use a mathematical formula to determine the minimum number of people who must be counted to constitute a representative sample of the total population. For example, if the total population is 1,000 people, only 150 of them may need to be surveyed directly. Processor 104 may take information from the representative sample and extrapolate it to the full population. In a non-limiting example, if 10 percent of the people in the sample are left-handed, it can be assumed that 100 out of a population of 1,000 are left-handed. Population sampling can actually return more accurate results than full enumeration or census, but there are some caveats. All population sampling have a margin of error, because there's always a chance that the sample selected for the survey differs from the total population in some way. The larger the sample size, the lower the margin of error might be.

With continued reference to FIG. 1, Population data 112 may additionally include statistical markup data 116. As used in the current disclosure, "statistical markup data" is information that describes the demographics of people accounted for in population data. Statistical markup data 116 may include information about the quantity or percentage of each demographic included within population data. Demographics may include but are not limited to age, sex, weight, height, marital status, clothing sizes, waist circumference, race, income, conicity index, energy score, nutrient band, employments, ethnicity, pregnancy status, lactation status, health, activity levels, handicap, and the like of persons within the population. In a non-limiting example, statistical markup data 116 may state that 48% of a given population is female. In another non-limiting example, statistical markup data 116 may include data stating that 12% of a population is between the ages of 18-24. An additional non-limiting example of a statistical markup data 116 may include data stating that 5% of a population is between 5' 7"-5' 10" and has a waist circumference of 36"-40".

With continued reference to FIG. 1, statistical markup data 116 may comprise a plurality of demographic categories. As used in the current disclosure, a "demographic category" is group generated as a function of one or more demographics. In embodiments, demographic categories may be generated as function of any two or more demographics of people. In embodiments, this demographic, Demographic categories may include an Energy score demographic, a conicity index demographic, and a micronutrient demographic. A energy score demographic may include all users within the same height range, weight range, activity level, and age range. A conicity index demographic may include height, weight, and waist circumference. A micronutrient demographic may include gender, age, pregnancy status, and lactation status.

With continued reference to FIG. 1, processor 104 may be configured to generate an energy score 120 as a function of the at least a statistical markup data 116. As used in the current disclosure, an "energy score" is a score used to reflect the energy of a certain demographic of people. In embodiments, the statistical markup data 116 may comprise an energy score demographic. As used in the current disclosure, "energy" is the level of vitality of a person over a given period. In embodiments, an energy score 120 may be reflected as a numerical score. In a non-limiting example, the numerical score may be a range from 0-3000, whereas 0 is very low energy and 3000 is extremely high energy. An energy score may be calculated as a function of an energy score formula, wherein the energy score formula comprises a basal metabolic rate multiplied by an activity multiplier. As used in current disclosure, a "basal metabolic rate" is the number of calories you burn as your body performs basic (basal) life-sustaining function. Commonly also termed as Resting Metabolic Rate (RMR), which is the calories burned if you stayed in bed all day. Your basal metabolic rate defines your basal metabolism rate which makes up about 60-70% of the calories humans use ("burn" or expend). This includes the energy your body uses to maintain the basic function of your living and breathing body, including heartbeat, cell production, respiration, maintenance of body temperature, circulation, nutrient processing, and the like. An activity multiplier may be calculated as a function of an activity rate. As used in current disclosure, a "activity rate" is the rating of how physically active a user is. In embodiments, an activity rate may be reflected as a numerical score. In a non-limiting example, the numerical score may be a range from 1-5, whereas 0 is very low physical activity and 5 is extremely physical activity energy. An activity multiplier may be assigned as a function of a activity level. In a non-limiting example, an activity multiplier may be directly correlated to the activity level of the user wherein an activity level of 1 may correlate to an activity multiplier of 1.2. An activity level of 2 may correlate to an activity multiplier of 1.357. An activity level of 3 may correlate to an activity multiplier of 1.55. An activity level of 4 may correlate to an activity multiplier of 1.725. An activity level of 5 may correlate to an activity multiplier of 1.9. Processor 104 may be designed and configured to create a machine-learning model using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm mounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

With continued reference to FIG. 1, processor 104 may be configured to generate a conicity index 124 as a function of the statistical markup data 116. As used in the current disclosure, an "conicity index" is an anthropometric measure which assesses the adiposity of a demographic. In embodiments, conicity index 124 may be calculated as a function of a statistical markup data 116, specifically a demographic category including a conicity index demographic. A conicity index 124 may be calculated using a conicity index formula, wherein the formula is as follows:

$$\text{Conicity Index} = \frac{\text{Waist circumference (m)}}{.109\sqrt{\frac{\text{weight (kg)}}{\text{height (m)}}}}$$

Conicity index may be calculated using any suitable measurement system, such as imperial and metric; the units provided in the formula above are merely exemplary. Once a conicity index 124 has been calculated processor 104 may sort the conicity index as a function of statistical markup data 116 including sex and as a function of a conicity index category. A conicity index category may include a three categories, wherein each category represents basic, balanced, and a high fat conicity index respectively. The basic category may be represented by a Conicity index 124 of less than 1.18 for males and less than 1.17 for females. The Balanced category may be represented by a conicity index 124 range of 1.19-1.35 for males and 1.18-1.35 for females. The High fat category is represented by a conicity index 124 above 1.36 for both males and females.

With continued reference to FIG. 1, processor 104 may be configured to generate an micronutrient band 128 as a function of the at least a statistical markup data 116. As used in the current disclosure, a "micronutrient band" is a quantity of micronutrients that is needed by a certain demographic group. In embodiments, micronutrient band 128 may be calculated as a function of a statistical markup data 116. Micronutrients are nutrients such as vitamins and minerals required by organisms in varying quantities throughout life to orchestrate a range of physiological functions to maintain health. Examples of micronutrients include but are not limited to Calcium, Sulfur, Phosphorus, Magnesium, Sodium, Potassium, Iron. Zinc, Boron, Copper, Chromium, Selenium, Manganese, Molybdenum, Cobalt, Fluorine, Iodine, Vitamin B complex, Vitamin C (Ascorbic acid), and the like.

With continued reference to FIG. 1, a processor 104 may calculate an micronutrient band 128 using a lookup table. A "lookup table," for the purposes of this disclosure, is an array of data that maps input values to output values. A lookup table may be used to replace a runtime computation with an array indexing operation. In another non limiting example, a micronutrient band look up table may be able to relate micronutrient band demographic to an micronutrient band 128. As used in the current disclosure, a "micronutrient demographic" includes demographics including gender, age, pregnancy status, and lactation status. In a non-limiting example, a micronutrient demographic may include males 14-18, females 31-50, pregnant females older than 19. A micronutrient band lookup table may relate statistical markup data 116 or demographic category to the micronutrient needs of said demographic. Processor 104 may be configured to "lookup" one or more micronutrient bands 128 for one or more demographic groups, in order to find a corresponding micronutrient band 128.

With continued reference to FIG. 1, processor 104 is configured to determine a plurality of alimentary data 132 of a user. As used in this disclosure, "alimentary data," is a quantity of at least a nutrient that is recommended for health of a given demographic. Nutrient may refer to, without limitation, macronutrients, such as protein, including non-essential amino acids, essential amino acids, fats including non-essential fats, essential fats such as long-chain polyunsaturated fatty acids (LC-PUFAs), short-chain polyunsaturated fatty acids (SC-PUFAs), omega fatty acids, carbohydrates, including digestible and non-digestible carbohydrates such as dietary fiber, inulin, *psyllium*, and methylcellulose; micronutrients, such as vitamin A, thiamin (vitamin B1), riboflavin (vitamin B2), niacin (vitamin B3), pantothenic acid (vitamin B5), vitamin B6, biotin (vitamin B7), folate (vitamin B12), vitamin C, vitamin D2, vitamin D3, vitamin E, vitamin K1, vitamin K2; minerals such as calcium, phosphorous, potassium, sodium, magnesium; trace elements such as iron, sulfur, manganese, selenium, chromium, molybdenum, copper, cobalt; halides such a chloride and iodine; electrolytes and salts including bicarbonate, creatine, and phosphocreatine; caloric content, or any other substance that provides nourishment essential for growth and maintenance of a user. In embodiments, processor 104 may calculate alimentary data 132 as a function of an energy score 120, conicity index 124, and/or a micronutrient band 128. Processor 104 may calculate alimentary data 132 using a lookup table. In another non limiting example, a nutrient look up table may be able to relate energy score 120, conicity index 124, and/or a micronutrient band 128 to alimentary data 132. Processor 104 may be configured to "lookup" one or more of energy score 120, conicity index 124, and/or a micronutrient band 128 for one or more demographic groups, in order to find a corresponding alimentary data 132.

With continued reference to FIG. 1, Processor 104 may be designed and configured to receive plurality of alimentary data 132 from another device. Alternatively or additionally, processor 104 may generate plurality of alimentary data 132 by receiving at least a biological extraction and generate plurality of alimentary data 132 as a function of at least a biological extraction. A "biological extraction," as used in this disclosure may refer to any biomarker, genetic or epigenetic indication, microbiome, or any chemical, biological, or physiological markers of data of a user, including for instance, and without limitation, as described in U.S. Non-provisional application Ser. No. 16/865,740, filed on May 4, 2020, and entitled "METHODS AND SYSTEMS FOR SYSTEM FOR NUTRITIONAL RECOMMENDATION USING ARTIFICIAL INTELLIGENCE ANALYSIS FOR IMMUNE IMPACTS," the entirety of which is incorporated herein by reference.

Continuing in reference to FIG. 1, processor 104 generating a alimentary data 132 may additionally include identifying a nutrition deficiency within a demographic category. As used in this disclosure, a "nutrition deficiency," is a calculated value that corresponds to any deficit in a nutrient value between a alimentary data and the current nutrition of the group. As a non-limiting example, detecting a nutrition deficiency may include calculating the deficiency using nutrition machine learning model, that inputs alimentary data 132 and outputs a nutritional deficiency. A processor 104 may use alimentary data 132 to calculate a nutritional deficiency of a user, for instance in non-limiting examples, by calculating a difference between a alimentary data 132 and the nutrition of the demographic group.

With continued reference to FIG. 1, processor 104 may be configured to generate alimentary data 132 using a nutrition machine learning model. As used in the current disclosure, a "nutrition machine learning model" is a mathematical and/or algorithmic representation of a relationship between inputs and outputs. A nutrition machine learning model may be implemented in any manner described in this disclosure regarding implementing and/or training machine learning models. Inputs to the machine learning model may include, as a non-limiting example, geofence 108, population data 112, statistical markup data 116, demographic categories, energy score 120, conicity index 124, a micronutrient band 128, any combination thereof. Outputs of the nutrition machine learning model may include a alimentary data 132 and identification of a nutritional deficiency. Inputs to the machine learning model may be received from a database, such as nutrient database 300. Nutrition machine learning model may by trained using nutrition training data. Nutrition training data may include a plurality of data entries containing a plurality of inputs that are correlated to a plurality of outputs for training a processor 104 by a machine-learning process. Nutrition training data may correlate the conicity index 124 of a demographic group of as inputs to the alimentary data 132 and nutritional deficiencies of a demographic group as an output. Nutrition training data may correlate the micronutrient band 128 and energy score 120 of a demographic group of as inputs to the alimentary data 132 of a demographic group as an output. Nutrition training data may include geofence 108, population data 112, statistical markup data 116, demographic categories, energy score 120, conicity index 124, a micronutrient band 128, any combination thereof, or the like. Nutrition training data may be stored in a database, such as a training data database, or remote data storage device, or a user input or device.

With continued reference to FIG. 1, a processor 104 may be configured to determine a plurality of phenotype clusters 136 as a function of the energy score, the micronutrient band, and/or the conicity index. As used in the current disclosure, a "phenotype cluster" is one or more demographic categories of people who share similar alimentary data. In embodiments, phenotype clusters 136 may be used to ensure that alimentary programs 140 meet the alimentary data of a high number of phenotypes at once. Phenotype Clusters 136 can be designed by grouping demographic groups by certain characteristics in which nutrient targets are not significantly different. In embodiments, phenotype clusters 136 may be generated using a phenotype classifier. Non-limiting examples of phenotype clusters are as follows:

| Phenotype Clusters | | | | |
|---|---|---|---|---|
| | Age (Years) | Sex | Conicity Index | Macro |
| 1 | 2-3 | M/F | N/A | N/A |
| 2 | 4-8 | M/F | N/A | N/A |
| 3 | 9-13 | M | Basic | 55/30/15 |
| 4 | 9-13 | M | Balanced | 40/30/30 |
| 5 | 9-13 | F | Basic | 55/30/15 |
| 6 | 9-13 | F | Balanced | 20/60/20 |
| 7 | 14-18 | M | Basic | 55/30/15 |
| 8 | 14-18 | M | Balanced | 40/30/30 |
| 9 | 14-18 | M | High Fat | 20/60/20 |
| 10 | 14-18 | F | Basic | 55/30/15 |
| 11 | 14-18 | F | Balanced | 40/30/30 |
| 12 | 14-18 | F | High Fat | 20/60/20 |
| 13 | 19-30 | M | Basic | 55/30/15 |
| 14 | 19-30 | M | Balanced | 40/30/30 |
| 15 | 19-30 | M | High Fat | 20/60/20 |
| 16 | 19-30 | F | Basic | 55/30/15 |
| 17 | 19-30 | F | Balanced | 40/30/30 |
| 18 | 19-30 | F | High Fat | 20/60/20 |
| 19 | 31-50 | M | Basic | 55/30/15 |
| 20 | 31-50 | M | Balanced | 40/30/30 |
| 21 | 31-50 | M | High Fat | 20/60/20 |
| 22 | 31-50 | F | Basic | 55/30/15 |
| 23 | 31-50 | F | Balanced | 40/30/30 |
| 24 | 31-50 | F | High Fat | 20/60/20 |
| 25 | 51-70 | M | Basic | 55/30/15 |
| 26 | 51-70 | M | Balanced | 40/30/30 |
| 27 | 51-70 | M | High Fat | 20/60/20 |
| 28 | 51-70 | F | Basic | 55/30/15 |
| 29 | 51-70 | F | Balanced | 40/30/30 |
| 30 | 51-70 | F | High Fat | 20/60/20 |
| 31 | <19 | F (Lac) | Basic | 55/30/15 |
| 32 | <19 | F (Lac) | Balanced | 40/30/30 |
| 33 | >19 | F (Lac) | Basic | 55/30/15 |
| 34 | >19 | F (Lac) | Balanced | 40/30/30 |

With continued reference to FIG. 1, processor 104 may be configured to generate a phenotype clusters 136 as a function a of a phenotype classifier. As used in the current disclosure, a "phenotype classifier" is a machine-learning model that sorts inputs into categories or bins of data, outputting the categories or bins of data and/or labels associated therewith. Phenotype classifier may be consistent with the classifier described below in FIG. 2. Inputs to the to the phenotype classifier may include, as a non-limiting example, geofence 108, population data 112, statistical markup data 116, demographic categories, energy score 120, conicity index 124, a micronutrient band 128, alimentary data 132, any combination thereof, or the like. The output to the phenotype classifier may be a phenotype cluster 136 that is specific to a given geofenced area. Phenotype training data is a plurality of data entries containing a plurality of inputs that are correlated to a plurality of outputs for training a processor by a machine-learning process to align and classify alimentary data 132 to a plurality of a demographic categories. Phenotype training data may be received from a database. Phenotype training data may contain as input, as a non-limiting examples, geofence 108, population data 112, statistical markup data 116, demographic categories, energy score 120, conicity index 124, a micronutrient band 128, alimentary data 132, any combination thereof, or the like. Phenotype training data may be generated from any past phenotype clusters 136. Phenotype training data may correlate an example of a phenotype cluster 136 to an example of a alimentary data 132. The "example of a phenotype clusters 136" and the "example of alimentary data 132" may be a prior phenotype clusters 136 and a alimentary data 132, respectively. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With continued reference to FIG. 1, a classifier, such as phenotype classifier, may be implemented as a fuzzy inferencing system. As used in the current disclosure, a "fuzzy inference" is a method that interprets the values in the input vector (i.e., statistical markup data and alimentary data 132.) and, based on a set of rules, assigns values to the output vector. A set of fuzzy rules may include a collection of linguistic variables that describe how the system should make a decision regarding classifying an input or controlling an output. An example of linguistic variables may include variables that represent a phenotype clusters 136. Examples of this may include two variables, one representing a demographic category and a second variable representing alimentary data 132.

Still referring to FIG. 1, processor may be configured to generate a machine learning model, such as phenotype classifier, using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

Still referring to FIG. 1, processor may be configured to generate a machine learning model, such as phenotype classifier, using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number experience of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With continued reference to FIG. 1, a processor 104 may be configured to generate a alimentary program 140 as a function of the alimentary data 132 and the plurality of phenotype clusters 136. As used in the current disclosure, a "alimentary program" comprises instructions for preparing a meal that fulfills the nutritional requirements of a demographic category. A alimentary program 140 may include both an ingredient combination and preparation instructions. Generating alimentary program 140 may include generating an ingredient combination. As used in the current disclosure, an "ingredient combination" comprises one or more foods, spices, and/or condiments used to make a meal. An ingredient combination may include an ingredient and a quantity for those ingredients. The quantity of ingredients may be configured to be scaled as a function of the number of desired portions. In embodiments, processor 104 may identify the nutritional value of each ingredient as a function of the ingredients weight. This may be displayed as a function of percentage of compliance of the alimentary data 132. In some embodiments, processor 104 may be configured to identify one or more replacement ingredients within the ingredient combination. As used in the current disclosure, a "replacement ingredient" is an ingredient that is nutritionally similar to the ingredients prescribed within a ingredient combination. In embodiment, replacement ingredients may be used to adjust for allergies, religious beliefs, personal preferences, and/or taste preferences. In embodiments, breakfast, lunch, dinner, snack, may have a nutrient target assigned to them as a function of the alimentary data 132. In a non-limiting example, alimentary data 132 may prescribe that a demographic group intake 10g of protein for breakfast. An alimentary program 140 may be configured to accomplish this goal.

With continued reference to FIG. 1, processor 104 may be configured to generate alimentary program 140 using an alimentary machine learning model. As used in the current disclosure, a "alimentary machine learning model" is a mathematical and/or algorithmic representation of a relationship between inputs and outputs. A alimentary machine learning model may be implemented in any manner described in this disclosure regarding implementing and/or training machine learning models. Inputs to the machine learning model may include, as a non-limiting example, geofence 108, population data 112, statistical markup data 116, demographic categories, energy score 120, conicity index 124, a micronutrient band 128, alimentary data 132, phenotype clusters 136, or any combination thereof. Outputs of the alimentary machine learning model may include an alimentary program. Inputs to the machine learning model may be received from a database, such as nutrient database 300. Alimentary machine learning model may by trained using alimentary training data. Alimentary training data may include a plurality of data entries containing a plurality of inputs that are correlated to a plurality of outputs for training a processor 104 by a machine-learning process. Alimentary training data may correlate the alimentary data 132 and phenotype clusters 136 as inputs to the alimentary program 140 of a demographic group as an output. Alimentary training data may include geofence 108, population data 112, statistical markup data 116, demographic categories, energy score 120, conicity index 124, a micronutrient band 128, alimentary data 132, phenotype clusters 136, any combination thereof, or the like. Alimentary training data may be stored in a database, such as a training data database, or remote data storage device, or a user input or device.

Figure 2:
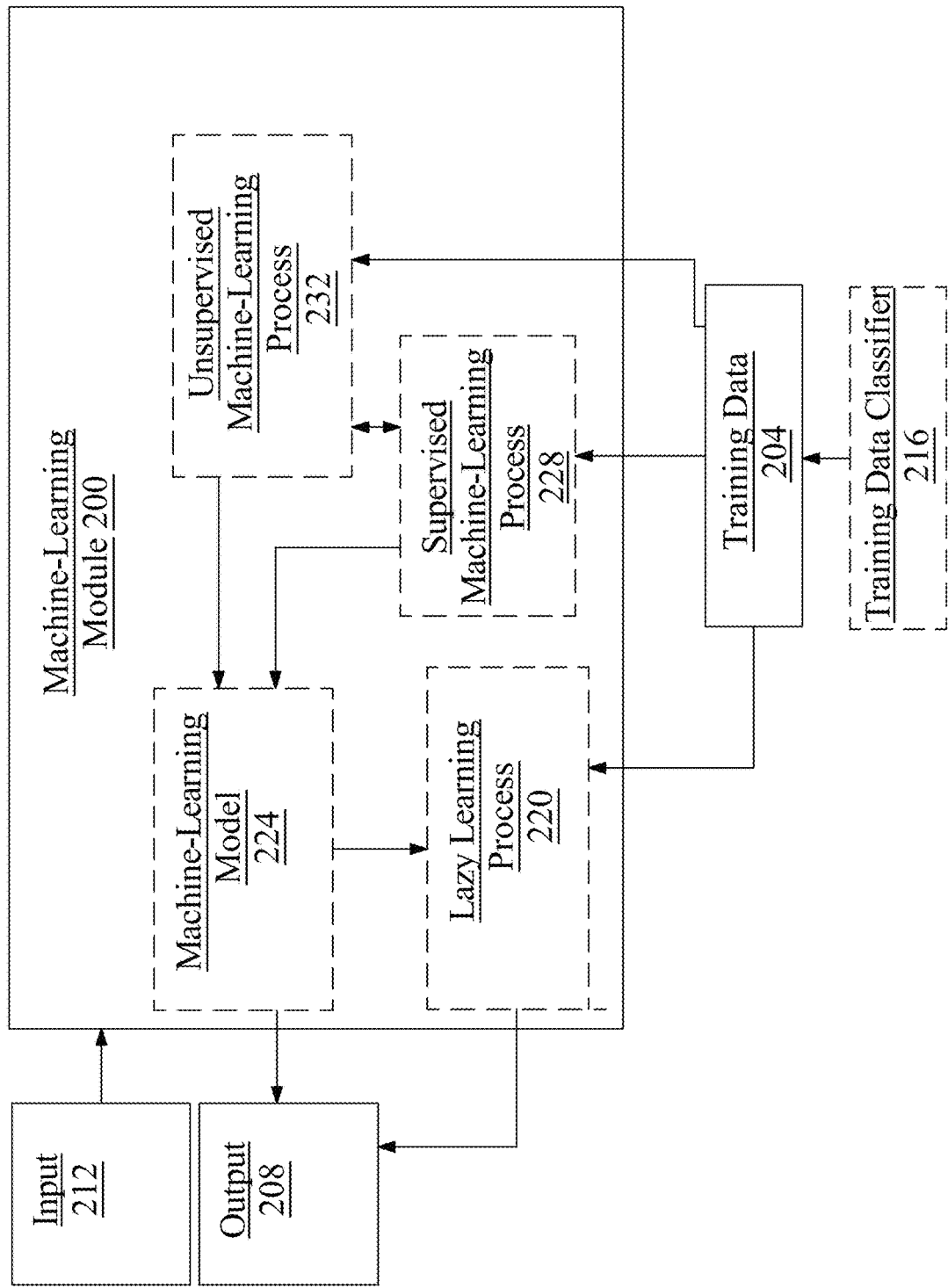
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively, or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine learning algorithm known as a "classification algorithm," as described in further detail below, that sorts of inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a alimentary data 132 or a conicity index 124 as described above as inputs, autonomous functions as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

For example, and still referring to FIG. 2, neural network also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes, one or more intermediate layers, and an output layer of nodes. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, a node may include, without limitation a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function $\varphi$, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above. In an embodiment, and without limitation, a neural network may receive semantic units as inputs and output vectors representing such semantic units according to weights $w_i$ that are derived using machine-learning processes as described in this disclosure.

Figure 3:
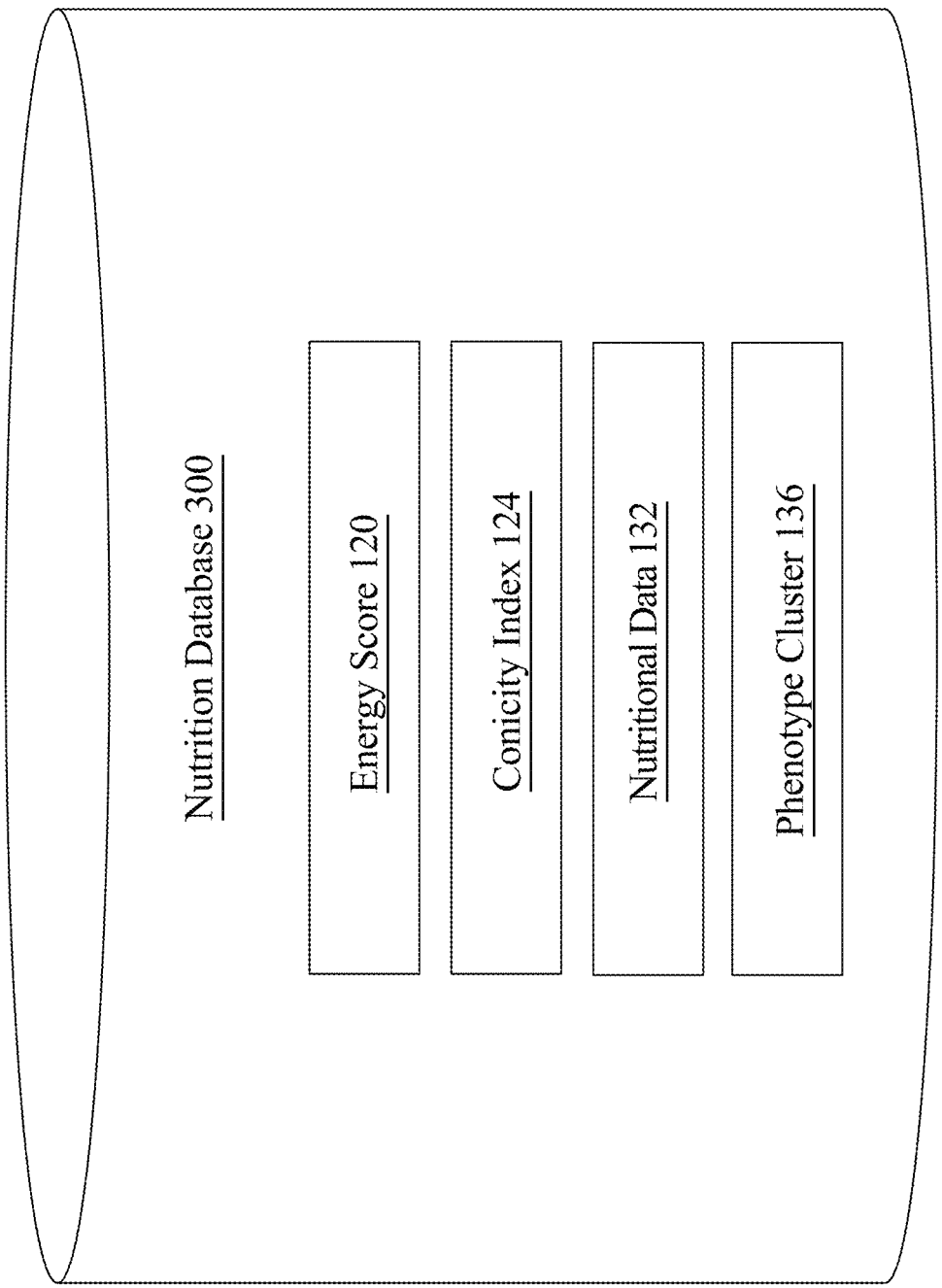
FIG. 3 is a block diagram of an exemplary embodiment of a nutrition database.

Now referring to FIG. 3, an exemplary nutrient database 300 is illustrated by way of block diagram. In an embodiment, geofence 108, population data 112, statistical markup data 116, demographic categories, energy score 120, conicity index 124, a micronutrient band 128, alimentary data 132, phenotype clusters 136, and the like may be stored in a nutrient database 300 (also referred to as "database"). Processor 104 may be communicatively connected with nutrient database 300. For example, in some cases, nutrient database 300 may be local to processor 104. Alternatively or additionally, in some cases, nutrient database 300 may be remote to processor 104 and communicative with processor 104 by way of one or more networks. Network may include, but not limited to, a cloud network, a mesh network, or the like. By way of example, a "cloud-based" system, as that term is used herein, can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connect directly, dynamically, and non-hierarchically to as many other computing devices as possible. A "network topology" as used in this disclosure is an arrangement of elements of a communication network. Nutrient database 300 may be implemented, without limitation, as a relational database, a key-value retrieval database such as a NOSQL database, or any other format or structure for use as a database that a person skilled in the art would recognize as suitable upon review of the entirety of this disclosure. Nutrient database 300 may alternatively or additionally be implemented using a distributed data storage protocol and/or data structure, such as a distributed hash table or the like. Nutrient database 300 may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Figure 4:
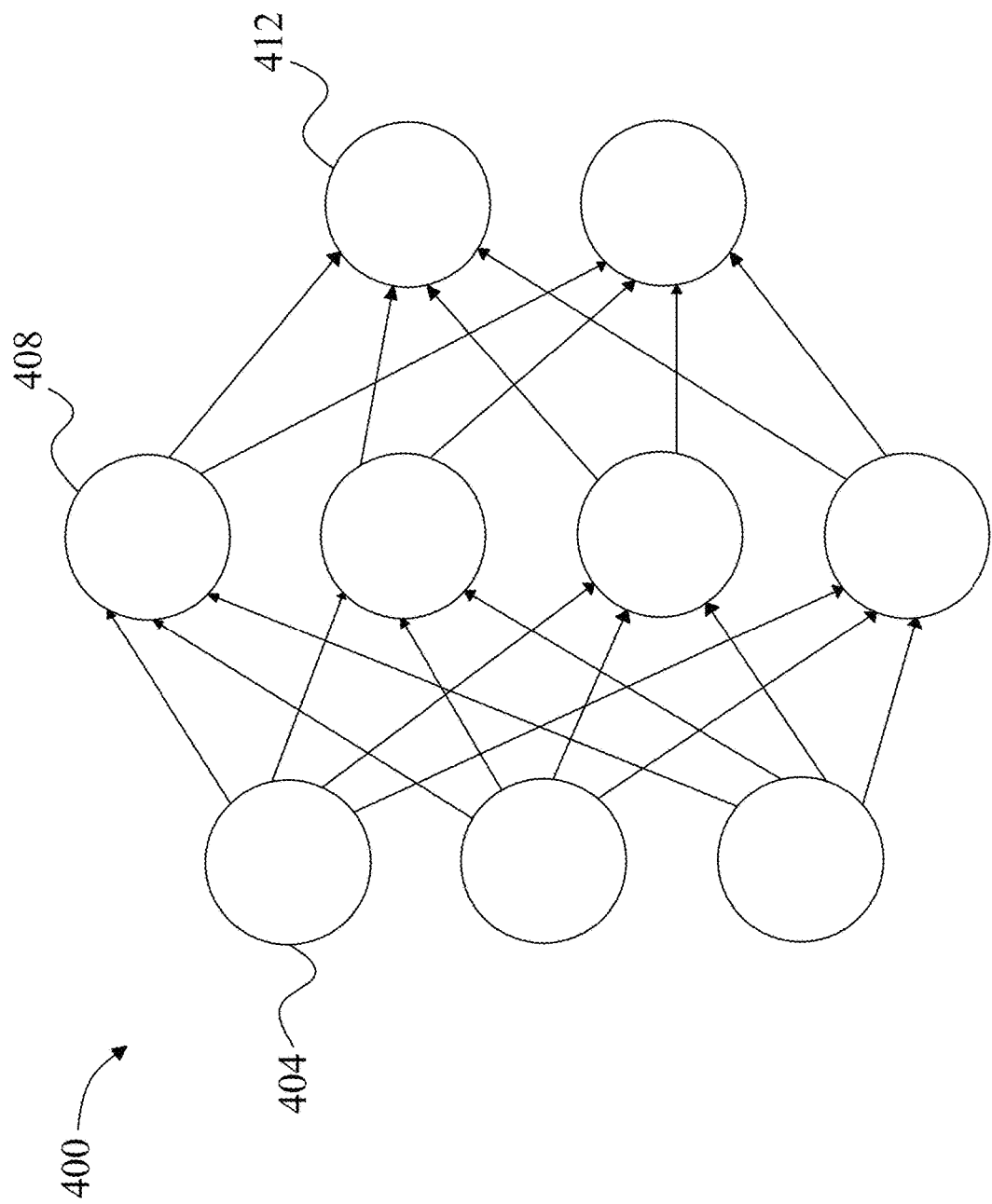
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
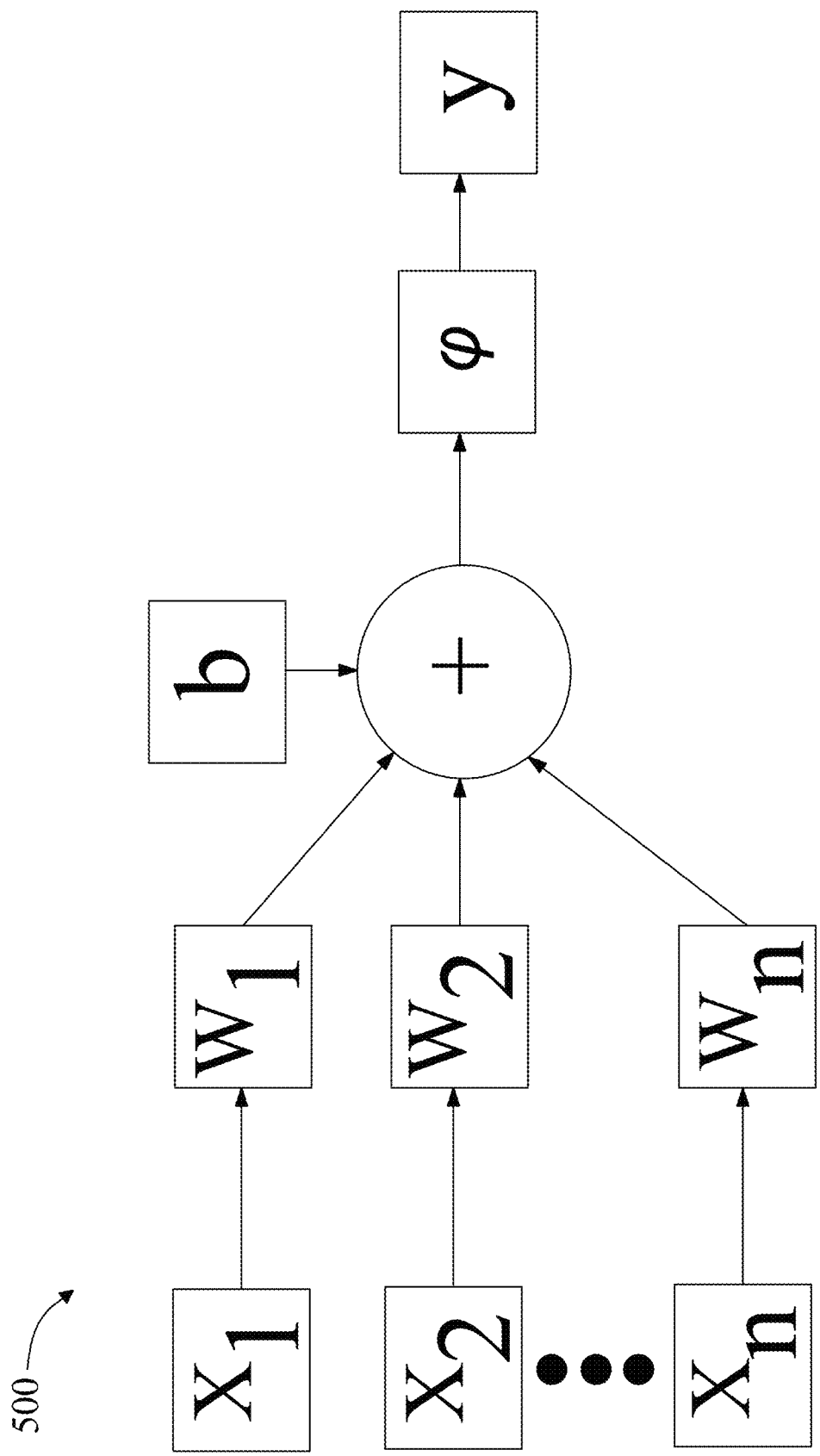
FIG. 5 is a diagram of an exemplary embodiment of a node of a neural network.

Referring now to FIG. 5, an exemplary embodiment of a node of a neural network is illustrated. A node may include, without limitation a plurality of inputs $x_i$ that may receive numerical values from inputs to a neural network containing the node and/or from other nodes. Node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 6:
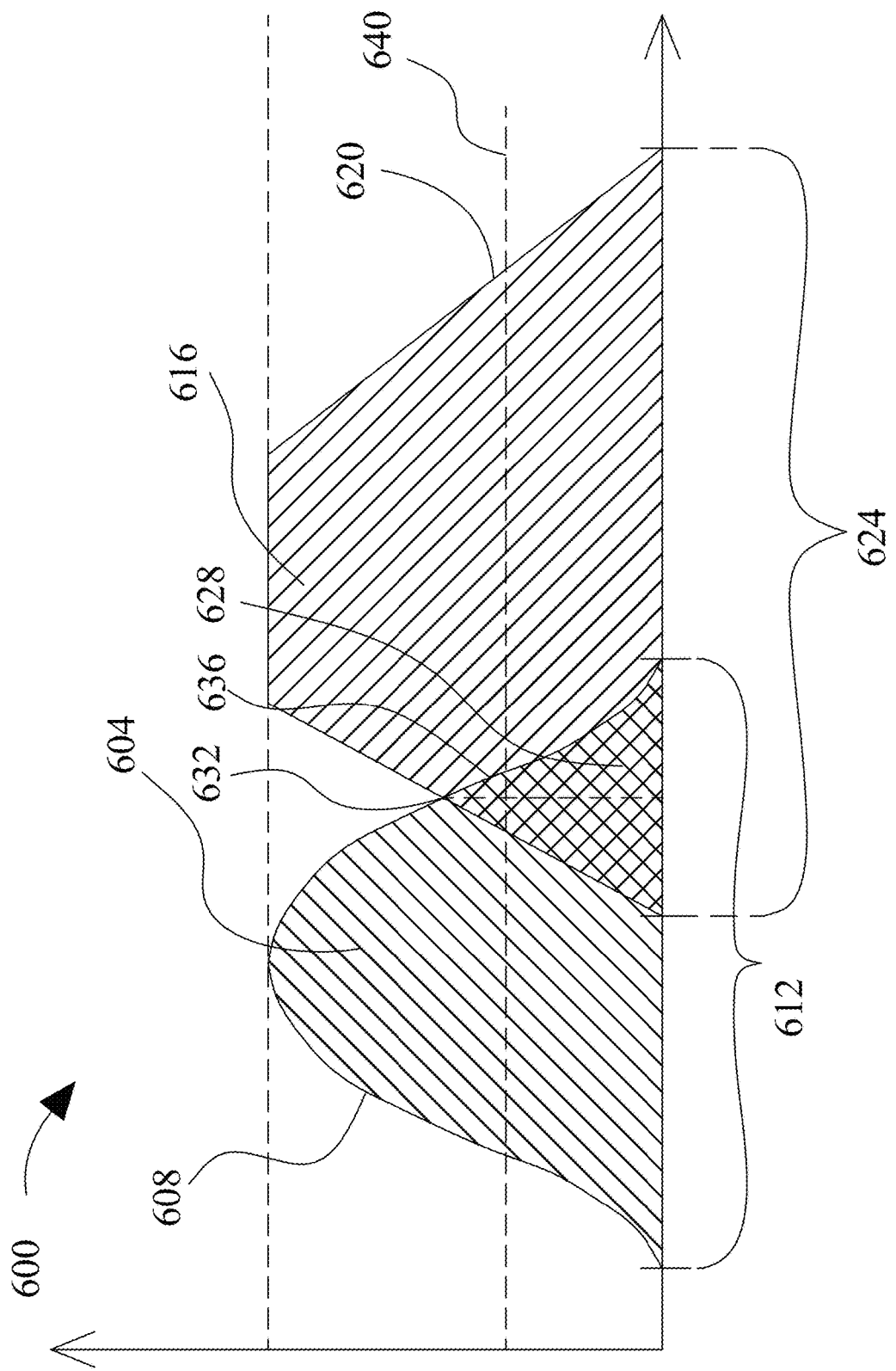
FIG. 6 is a graph illustrating an exemplary relationship between fuzzy sets.

Now referring to FIG. 6, an exemplary embodiment of fuzzy set comparison 600 is illustrated. In a non-limiting embodiment, the fuzzy set comparison. In a non-limiting embodiment, fuzzy set comparison 600 may be consistent with fuzzy set comparison in FIG. 1. In another non-limiting the fuzzy set comparison 600 may be consistent with the name/version matching as described herein. For example and without limitation, the parameters, weights, and/or coefficients of the membership functions may be tuned using any machine-learning methods for the name/version matching as described herein. In another non-limiting embodiment, the fuzzy set may represent user demographic categories, statistical markup data 116, energy score 120, conicity index 124, a micronutrient band 128, alimentary data 132, and the like from FIG. 1.

Alternatively or additionally, and still referring to FIG. 6, fuzzy set comparison 600 may be generated as a function of determining data compatibility threshold. The compatibility threshold may be determined by a computing device. In some embodiments, a computing device may use a logic comparison program, such as, but not limited to, a fuzzy logic model to determine the compatibility threshold and/or version authenticator. Each such compatibility threshold may be represented as a value for a phenotype cluster 136 representing the compatibility threshold, or in other words a fuzzy set as described above that corresponds to a degree of compatibility and/or allowability as calculated using any statistical, machine-learning, or other method that may occur to a person skilled in the art upon reviewing the entirety of this disclosure. In some embodiments, determining the compatibility threshold and/or version authenticator may include using a linear regression model. A linear regression model may include a machine learning model. A linear regression model may map statistics such as, but not limited to, frequency of the same range of version numbers, and the like, to the compatibility threshold and/or version authenticator. In some embodiments, determining the compatibility threshold of any phenotype cluster 136 may include using a classification model. A classification model may be configured to input collected data and cluster data to a centroid based on, but not limited to, frequency of appearance of the range of versioning numbers, linguistic indicators of compatibility and/or allowability, and the like. Centroids may include scores assigned to them such that the compatibility threshold may each be assigned a score. In some embodiments, a classification model may include a K-means clustering model. In some embodiments, a classification model may include a particle swarm optimization model. In some embodiments, determining a compatibility threshold may include using a fuzzy inference engine. A fuzzy inference engine may be configured to map one or more compatibility threshold using fuzzy logic. In some embodiments, a plurality of computing devices may be arranged by a logic comparison program into compatibility arrangements. A "compatibility arrangement" as used in this disclosure is any grouping of objects and/or data based on skill level and/or output score. Membership function coefficients and/or constants as described above may be tuned according to classification and/or clustering algorithms. For instance, and without limitation, a clustering algorithm may determine a Gaussian or other distribution of questions about a centroid corresponding to a given compatibility threshold and/or version authenticator, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Still referring to FIG. 6, inference engine may be implemented according to input and/or output. For instance, an acceptance variable may represent a first measurable value pertaining to the classification of conicity index 124, alimentary data 132 to a statistical markup data 116. Continuing the example, an output variable may represent a phenotype cluster 136 specific the demographic group. In an embodiment, conicity index 124, statistical markup data 116, and alimentary data 132 may be represented by their own fuzzy set. In other embodiment s, a phenotype cluster 136 specific to the user may be represented as a function of the intersection two or more fuzzy sets as shown in FIG. 6, An inference engine may combine rules, such as any semantic versioning, semantic language, version ranges, and the like thereof. The degree to which a given input function membership matches a given rule may be determined by a triangular norm or "T-norm" of the rule or output function with the input function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T(T(a, b), c)), and the requirement that the number 1 acts as an identity element. Combinations of rules ("and" or "or" combination of rule membership determinations) may be performed using any T-conorm, as represented by an inverted T symbol or "⊥," such as max(a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively or additionally, output rules may be replaced with functions according to the Takagi-Sugeno-King (TSK) fuzzy model.

A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 608 may represent a set of values within first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range 612 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, & \text{for } x > c \text{ and } x < a \\ \frac{x-a}{b-a}, & \text{for } a \le x < b \\ \frac{c-x}{c-b}, & \text{if } b < x \le c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}(\frac{x-c}{\sigma})^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

First fuzzy set 604 may represent any value or combination of values as described above, including any software component datum, any source repository datum, any malicious quantifier datum, any predictive threshold datum, any string distance datum, any resource datum, any niche datum, and/or any combination of the above. A second fuzzy set 616, which may represent any value which may be represented by first fuzzy set 604, may be defined by a second membership function 620 on a second range 624; second range 624 may be identical and/or overlap with first range 612 and/or may be combined with first range via Cartesian product or the like to generate a mapping permitting evaluation overlap of first fuzzy set 604 and second fuzzy set 616. Where first fuzzy set 604 and second fuzzy set 616 have a region 636 that overlaps, first membership function 608 and second membership function 620 may intersect at a point 632 representing a probability, as defined on probability interval, of a match between first fuzzy set 604 and second fuzzy set 616. Alternatively or additionally, a single value of first and/or second fuzzy set may be located at a locus 636 on first range 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a non-limiting example, represent a degree of match between first fuzzy set 604 and second fuzzy set 616, and/or single values therein with each other or with either set, which is sufficient for purposes of the matching process; for instance, and phenotype cluster 132 may indicate a sufficient degree of overlap between the alimentary data 132 and statistical markup data 116 for combination to occur as described above. There may be multiple thresholds. Each threshold may be established by one or more user inputs. Alternatively or additionally, each threshold may be tuned by a machine-learning and/or statistical process, for instance and without limitation as described in further detail below.

Figure 7:
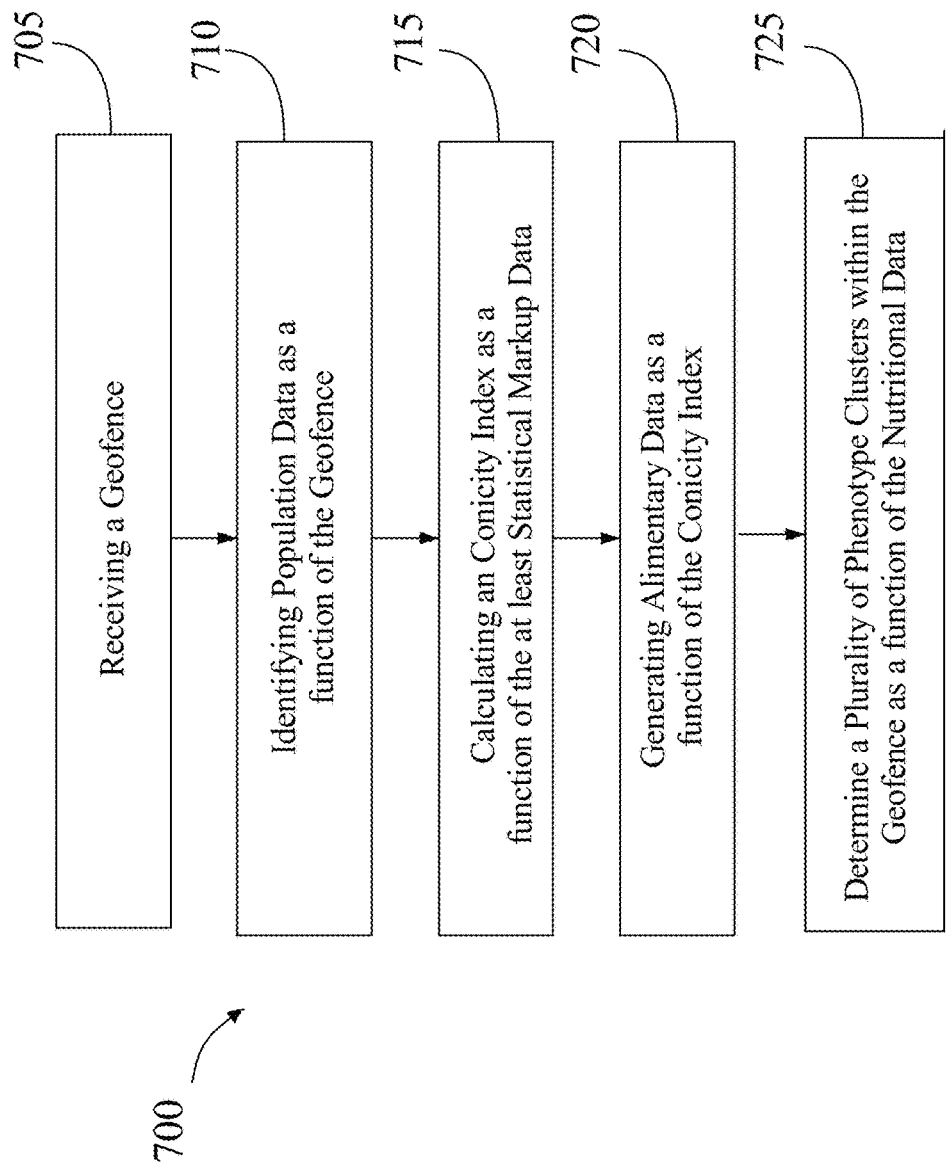
FIG. 7 is a flow diagram of an exemplary method for generating alimentary data within a geofence.

Referring to FIG. 7, an exemplary method 700 for generating alimentary data within a geofence. Method 700 incudes a step 705, of receiving, using at least a processor, a geofence, wherein the geofence comprises a predetermined geographic area. This may occur as described above in reference to FIGS. 1-6.

With continued reference to FIG. 7, method 700 includes a step 710 of identifying, using the at least a processor, population data as a function of the geofence, wherein the population data comprises at least a statistical markup data. This may occur as described above in reference to FIGS. 1-6.

With continued reference to FIG. 7, method 700 includes a step 715 of calculating, using the at least a processor, an conicity index as a function of the at least a statistical markup data. This may occur as described above in reference to FIGS. 1-6.

With continued reference to FIG. 7, method 700 includes a step 720 of generating, using the at least a processor, alimentary data as a function of the conicity index, wherein the alimentary data comprises a recommended nutritional intake. This may occur as described above in reference to FIGS. 1-6. In some embodiments, the method may include generating, using the at least a processor, a alimentary program as function of the alimentary data. Generating the alimentary program may comprise selecting an ingredient combination as a function of the recommended nutritional intake of the user. In other embodiments, generating the alimentary data additionally may include detecting at least a nutrition deficiency within the phenotype cluster. In embodiments, the alimentary data may be generated using a nutrient machine learning model.

With continued reference to FIG. 7, method 700 includes a step 725 of determining, using the at least a processor, a plurality of phenotype clusters within the geofence as a function of the alimentary data. This may occur as described above in reference to FIGS. 1-6. In embodiments, the plurality of phenotype clusters may be determined using a phenotype classifier.

With continued reference to FIG. 7, method 700 may include generating, using the at least a processor, a micronutrient band as a function of the at least a statistical markup data. Generating the alimentary data may include generating the alimentary data as function of the micronutrient band. In some embodiments, the method may include calculating, using the at least a processor, an energy score as a function of the at least a statistical markup data. Generating the alimentary data may additionally comprise generating the alimentary data as function of the energy score.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
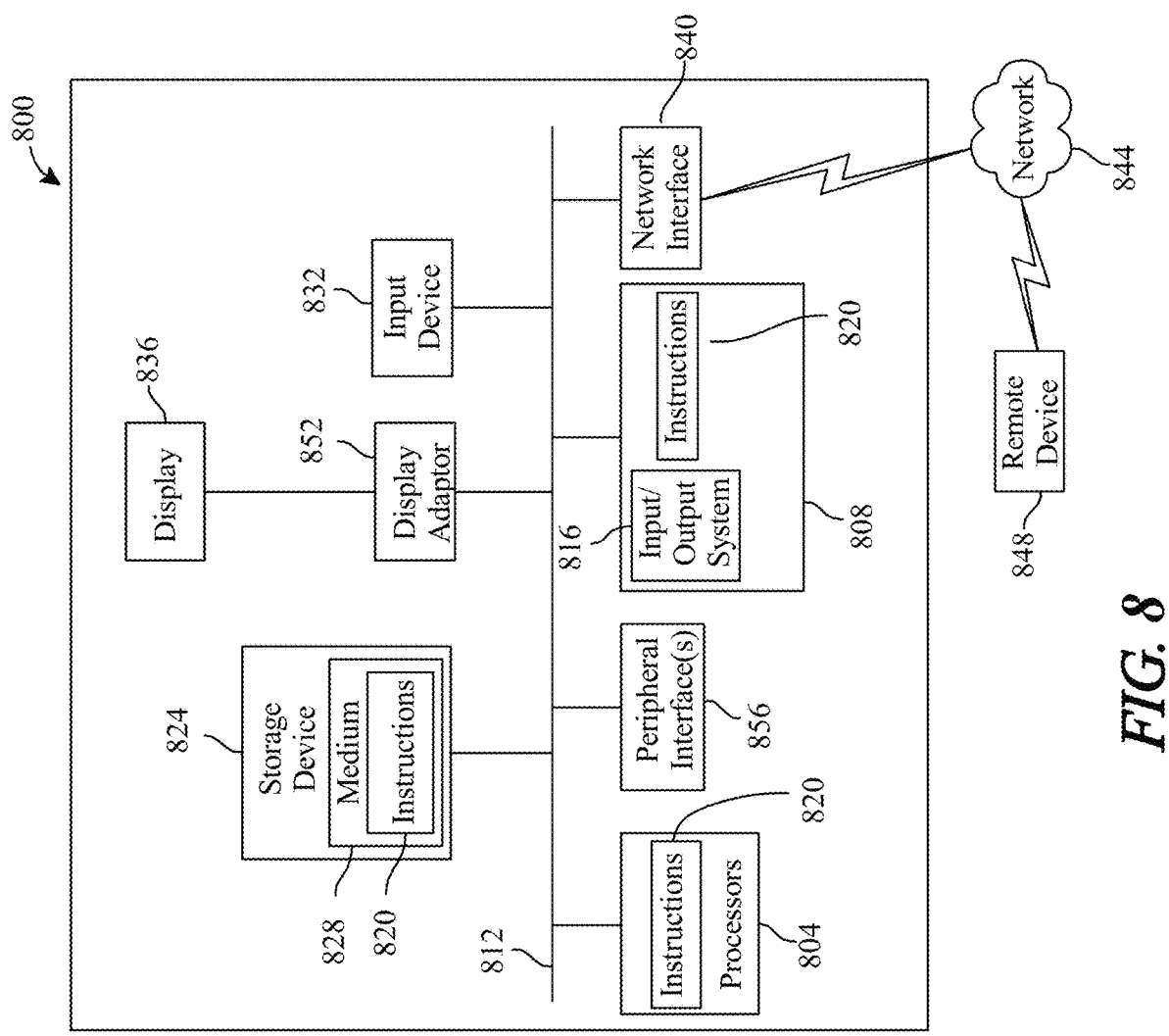
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIRE-WIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. An apparatus for generating alimentary data within a geofence; wherein the apparatus comprises:
   at least a processor; and
   a memory communicatively connected to the at least a processor, the memory containing instructions configuring the at least a processor to:
   receive a geofence, wherein the geofence comprises a predetermined geographic area;
   identify population data as a function of the geofence, wherein the population data comprises at least statistical makeup data;
   calculate a demographic conicity index as a function of the at least statistical makeup data;
   calculate an energy score as a function of the statistical makeup data;
   generate alimentary data as a function of a conicity index, wherein the alimentary data comprises a recommended nutrient intake, and wherein generating the alimentary data comprises:
   receiving nutrition training data, wherein the nutrition training data comprises at least the conicity index, at least a micronutrient band, and at least the energy score correlated to at least an alimentary datum;
   training a nutrition machine learning model using the nutrition training data, wherein training the nutrition machine learning model comprises:
   inputting the nutrition training data to an input layer of nodes of the nutrition machine learning model; and
   adjusting connections and weights between nodes in adjacent layers of the nutrition machine learning model;
   generating the alimentary data as a function of the trained nutrition machine learning model, wherein the demographic conicity index is provided to the trained nutrition machine learning model as an input to output the alimentary data;

retraining the nutrition machine learning model iteratively using outputs of previous iterations as inputs to subsequent iterations; and determine a plurality of phenotype clusters within the geofence as a function of the alimentary data, wherein determining the plurality of phenotype clusters further comprises:

receiving phenotype training data, wherein the phenotype training data comprises the alimentary data correlated to a phenotype cluster of the plurality of phenotype clusters;

training a phenotype classifier using the phenotype training data; and generating the plurality of phenotype clusters as a function of the trained phenotype classifier, wherein the alimentary data outputted from the trained nutrition machine learning model is provided as an input to the trained phenotype classifier to output the plurality of phenotype clusters;

generate an alimentary program as a function of the alimentary data and the plurality of phenotype clusters, wherein generating the alimentary program comprises selecting an ingredient combination as a function of the alimentary data; and identify one or more replacement ingredients within the ingredient combination, wherein the one or more replacement ingredients are nutritionally similar to the ingredients prescribed within the ingredient combination.

2. The apparatus of claim 1, wherein generating the alimentary data additionally comprises detecting at least a nutrition deficiency.

3. The apparatus of claim 1, wherein the memory contains instructions further configuring the at least a processor to generate a micronutrient band as a function of the statistical makeup data.

4. The apparatus of claim 3, wherein generating the alimentary data comprises generating the alimentary data as a function of the micronutrient band.

5. The apparatus of claim 1, wherein generating the alimentary data comprises generating the alimentary data as a function of the energy score.

6. A method for generating alimentary data within a geofence, wherein the method comprises:

receiving, using at least a processor, a geofence, wherein the geofence comprises a predetermined geographic area;

identifying, using the at least a processor, population data as a function of the geofence, wherein the population data comprises at least a statistical makeup data;

calculating, using the at least a processor, a demographic conicity index as a function of the at least a statistical makeup data;

calculating an energy score as a function of the statistical makeup data;

generating, using the at least a processor, alimentary data as a function of a conicity index, wherein the alimentary data comprises a recommended nutrient intake, and wherein generating the alimentary data comprises:

receiving nutrition training data, wherein the nutrition training data comprises at least the conicity index, at least a micronutrient band, and at least the energy score correlated to at least an alimentary datum;

training a nutrition machine learning model using the nutrition training data, wherein training the nutrition machine learning model comprises:

inputting the nutrition training data to an input layer of nodes of the nutrition machine learning model; and adjusting connections and weights between nodes in adjacent layers of the nutrition machine learning model;

generating the alimentary data as a function of the trained nutrition machine learning model, wherein the demographic conicity index is provided to the trained nutrition machine learning model as an input to output the alimentary data; and retraining the nutrition machine learning model iteratively using outputs of previous iterations as inputs to subsequent iterations; and determining, using the at least a processor, a plurality of phenotype clusters within the geofence as a function of the alimentary data, wherein determining the plurality of phenotype clusters further comprises:

receiving phenotype training data, wherein the phenotype training data comprises the alimentary data correlated to a phenotype cluster of the plurality of phenotype clusters;

training a phenotype classifier using the phenotype training data; and generating the plurality of phenotype clusters as a function of the trained phenotype classifier, wherein the alimentary data outputted from the trained nutrition machine learning model is provided as an input to the trained phenotype classifier to output the plurality of phenotype clusters;

generating an alimentary program as a function of the alimentary data and the plurality of phenotype clusters, wherein generating the alimentary program comprises selecting an ingredient combination as a function of the alimentary data; and identifying one or more replacement ingredients within the ingredient combination, wherein the one or more replacement ingredients are nutritionally similar to the ingredients prescribed within the ingredient combination.

7. The method of claim 6, wherein generating the alimentary data additionally comprises detecting at least a nutrition deficiency within the phenotype cluster.

8. The method of claim 6, further comprising generating, using the at least a processor, a micronutrient band as a function of the at least a statistical makeup data.

9. The method of claim 8, wherein generating the alimentary data comprises generating the alimentary data as a function of the micronutrient band.

10. The method of claim 6, wherein generating the alimentary data comprises generating the alimentary data as a function of the energy score.

* * * * *